(12) United States Patent
Phipps et al.

(10) Patent No.: US 7,212,853 B1
(45) Date of Patent: May 1, 2007

(54) ELECTROTRANSPORT AGENT DELIVERY METHOD AND APPARATUS

(75) Inventors: J. Bradley Phipps, Sunnyvale, CA (US); Gary A. Lattin, Nemo, SD (US); Ronald P. Haak, Palo Alto, CA (US); Felix Theeuwes, Los Altos Hills, CA (US); Suneel K. Gupta, Sunnyvale, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 08/952,368

(22) PCT Filed: Jun. 7, 1996

(86) PCT No.: PCT/US96/09989

§ 371 (c)(1),
(2), (4) Date: Nov. 17, 1997

(87) PCT Pub. No.: WO96/40364

PCT Pub. Date: Dec. 19, 1996

(51) Int. Cl.
*A61N 1/30* (2006.01)

(52) U.S. Cl. ...................................... 604/20
(58) Field of Classification Search ............... 604/501, 604/20, 50, 19; 607/149, 152; 210/660, 210/681
See application file for complete search history.

(56) References Cited

U.S. PATENT DOCUMENTS

| | | | |
|---|---|---|---|
| 4,250,878 A | 2/1981 | Jacobsen et al. | |
| 4,301,794 A * | 11/1981 | Tapper | 604/501 |
| 4,340,047 A | 7/1982 | Tapper et al. | |
| 4,383,529 A | 5/1983 | Webster | |
| 4,474,570 A | 10/1984 | Ariura et al. | |
| 4,722,726 A | 2/1988 | Sanderson et al. | |
| 4,752,285 A | 6/1988 | Petelenz et al. | |
| 4,822,334 A * | 4/1989 | Tapper | 604/20 |
| 4,822,802 A | 4/1989 | Levy et al. | |
| 4,878,892 A | 11/1989 | Sibalis et al. | |
| 5,019,034 A | 5/1991 | Weaver et al. | |
| 5,042,975 A * | 8/1991 | Chien et al. | 604/20 |
| 5,047,007 A | 9/1991 | McNichols et al. | |

(Continued)

FOREIGN PATENT DOCUMENTS

DE  410009  5/1934

(Continued)

OTHER PUBLICATIONS

Bagniefski et al. "A Comparison of Pulsed and Continuous Current Iontophoresis", *Journal of Controlled Release*, 113-122 (1990).

(Continued)

*Primary Examiner*—Manuel Mendez
(74) *Attorney, Agent, or Firm*—Woodcock Washburn LLP

(57) ABSTRACT

An electrotransport agent delivery device (10) for delivering a therapeutic agent through intact skin, and a method of operating same, is provided. The device applies a pulsing electrotransport current wherein current pulses have a magnitude above a critical level ($I_c$) at which the skin is transformed into a higher electrotransport delivery efficiency (E) state. Most preferably the length of the applied current pulses is at least 5 msec and preferably at least 10 msec.

26 Claims, 8 Drawing Sheets

U.S. PATENT DOCUMENTS

| | | | |
|---|---|---|---|
| 5,080,646 A | 1/1992 | Theeuwes et al. | |
| 5,125,894 A | 6/1992 | Phipps et al. | |
| 5,135,477 A | 8/1992 | Untereker et al. | |
| 5,135,478 A | 8/1992 | Sibalis | |
| 5,203,768 A * | 4/1993 | Haak et al. | 604/20 |
| 5,224,927 A * | 7/1993 | Tapper | 604/20 |
| 5,232,438 A | 8/1993 | Theeuwes et al. | |
| 5,298,017 A * | 3/1994 | Theeuwes et al. | 604/20 |
| 5,374,242 A | 12/1994 | Haak et al. | |
| 5,443,442 A | 8/1995 | Phipps et al. | |
| 5,853,383 A * | 12/1998 | Murdock | 604/20 |
| 5,919,155 A * | 7/1999 | Lattin et al. | 604/20 |
| 5,983,130 A | 11/1999 | Phipps et al. | |
| 6,718,201 B1 | 4/2004 | Phipps et al. | |

FOREIGN PATENT DOCUMENTS

| | | | |
|---|---|---|---|
| EP | 0547482 A | 6/1993 | |
| WO | WO 8808729 | 11/1988 | |
| WO | WO-9115258 | * 10/1991 | |
| WO | WO 92/18197 A | 10/1992 | |
| WO | WO 9527530 | 10/1995 | |

OTHER PUBLICATIONS

Burnette, R., et al. "Influence of Constant Current Iontophoresis on the Impedance and Passive $Na^+$ Permeability of Excised Nude Mouse Skin", 77 *J. Pharmaceutical Sciences* 492 (1988).

Pikal et al, "Study of the Mechanisms of Flux Enhancement Through Hairless Mouse Skin by Pulsed DC Iontophoresis", 8 *Pharmaceutical Research* 365 (1991).

* cited by examiner

ELECTROTRANSPORT AGENT DELIVERY METHOD AND APPARATUS

CROSS REFERENCE TO RELATED APPLICATIONS

This application is the National Stage of International Application No. PCT/US96/09989, filed Jun. 7, 1996, which claims priority from U.S. Ser. No. 08/483,069, filed Jun. 7, 1995, now U.S. Pat. No. 5,983,130, issued Nov. 9, 1999.

TECHNICAL FIELD

The present invention generally concerns a method and apparatus for the electrically assisted delivery of a therapeutic agent (e.g., a drug) through a body surface (e.g., intact skin) at increased efficiency. This invention is particularly applicable to the electrotransport of highly potent therapeutic agents which are to be delivered at small dosage levels.

BACKGROUND OF THE INVENTION

The present invention concerns in vivo methods and apparatuses for transdermal electrotransport delivery of therapeutic agents, typically drugs. Herein the terms "electrotransport", "iontophoresis" and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (i.e., 100% ionized), completely uncharged, or partly charged and partly neutral. The therapeutic agent or species may be delivered by electromigration, electroosmosis or a combination of these processes. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force to a reservoir containing the therapeutic species.

As used herein, the terms "electrotransport", "iontophoresis" and "iontophoretic" refer to (1) the delivery of charged drugs or agents by electromigration, (2) the delivery of uncharged drugs or agents by the process of electroosmosis, (3) the delivery of species by transport processes which include an electroporation step (See, e.g., Weaver et al. U.S. Pat. No. 5,019,034), (4) the delivery of charged drugs or agents by the combined processes of electromigration and electroosmosis, and/or (5) the delivery of a mixture of charged and uncharged drugs or agents by the combined processes of electromigration and electroosmosis, combinations of the above processes to deliver either or both of charged or uncharged species.

Iontophoretic devices for delivering ionized drugs through the skin have been known since the early 1900's. See for example, Deutsch U.S. Pat. No. 410,009. In presently known electrotransport devices, at least two electrodes or electrode assemblies are used. Both electrodes/electrode assemblies are disposed so as to be in intimate electrical contact with some portion of the skin of the body. One electrode, called the active or donor electrode, is the electrode from which the ionic substance, agent, medicament, drug precursor or drug is delivered into the body through the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode.

As is discussed above, electrotransport delivery devices can be used to deliver uncharged drugs or agents into the body, e.g, transdermally. This is accomplished by a process called electroosmosis. Electroosmosis is the (e.g., transdermal) flux of a liquid solvent (e.g., the liquid solvent containing the uncharged drug or agent) which is induced by the presence of an electric field imposed across the skin by the donor electrode.

Electrotransport electrode assemblies/devices generally include a reservoir or source of the beneficial agent or drug (preferably an ionized or ionizable species or a precursor of such species), which is to be delivered into the body by electrotransport. Examples of such reservoirs or sources include a pouch as described in Jacobsen U.S. Pat. No. 4,250,878, a pre-formed gel body as disclosed in Webster U.S. Pat. No. 4,382,529 and Ariura, et al. U.S. Pat. No. 4,474,570 and a receptacle containing a liquid solution as disclosed in Sanderson, et al. U.S. Pat. No. 4,722,726. Such drug reservoirs are connected to the anode or the cathode of an electrotransport device to provide a fixed or renewable source of one or more desired species or agents. Electrical current is typically applied to the reservoir by means of a current distributing member, which may take the form of a metal plate, a foil layer, a conductive screen, or a polymer film loaded with an electrically conductive filler such as silver or carbon particles. The current distributing member, including any appropriate connectors and associated connective conductors such as leads, and the reservoir comprise an electrode assembly herein.

The prior art has recognized that "competitive" ionic species having the same charge (i.e., the same sign) as the drug ions being delivered by electrotransport have a negative impact on electrotransport drug delivery efficiency. The efficiency (E) of electrotransport delivery of a particular species is defined herein as the rate of electrotransport delivery of that species per unit of applied electrotransport current (mg/mA-h). The prior art further recognized that competitive ionic species were inherently produced during operation of these devices. The competitive species produced are dependent upon the type of electrode material which is in contact with the drug solution. For example, if the electrode is composed of an electrochemically inert material (e.g., platinum or stainless steel), the electrochemical charge transfer reaction occurring at the electrode surface tended to be water electrolysis since water is the overwhelmingly preferred liquid solvent used in electrotransport drug solutions. Water electroysis produces competing hydronium ions at the anode (in the case of cationic electrotransport drug delivery) and competing hydroxyl ions at the cathode (in the case of anionic electrotransport drug delivery). On the other hand, if the electrode is composed of an electrochemically oxidizable or reducible species, then the electrode itself is oxidized or reduced to form a competitive ionic species. For example, Untereker et al U.S. Pat. No. 5,135,477 and Petelenz et al U.S. Pat. No. 4,752,285 recognize that competitive ionic species are electrochemically generated at both the anode and cathode of an electrotransport delivery device. In the case of an electrotransport delivery device having a silver anodic donor electrode, application of current through the silver anode causes the silver to become oxidized ($Ag \rightarrow Ag^+ + e^-$) thereby forming silver cations which compete with the cationic drug for delivery into the skin by electrotransport. The Untereker and Petelenz patents teach that providing a cationic drug in the form of a halide salt causes a chemical reaction which removes the "competing" silver ions from the donor solution (i.e., by reacting the silver ions with the halide counter ion of the drug to form a water insoluble silver halide precipitate; $Ag^+ + X^- \rightarrow AgX$), thereby achieving higher drug delivery efficiency. In addition to these patents, Phipps et al PCT/US95/04497 filed on Apr. 7, 1995 teaches the use of supplementary chloride ion sources in the form of high molecular weight chloride resins in the donor reservoir of a transdermal electrotransport delivery device. These resins are highly effective at providing sufficient chloride for preventing silver ion migration, yet because of the high molecular weight of the resin cation, the resin cation is effectively immobile and hence cannot compete with the drug cation for delivery into the body.

The prior art has long recognized that the application of electric current through skin causes the electrical resistance of the skin to decrease. See, for example, Haak et al U.S. Pat. No. 5,374,242 (FIG. 3). Thus, as the electrical resistance of the skin drops, lower voltages are needed to drive a particular level of electrotransport current through the skin. This same phenomenon is observed in a technique referred to as "electroporation" of the skin. See Weaver et al U.S. Pat. No. 5,019,034. Electroporation involves the application of short, high voltage electrical pulses to produce what is characterized as a transient (e.g., decreasing to normal levels in 10 to 120 sec. for excised frog skin) increase in tissue permeability. Electroporation is also characterized by the creation of pores in lipid membranes due to reversible electrical breakdown. Electroporation does not, itself, deliver any drug but merely prepares the tissue thereby treated for delivery of drug by any of a number of techniques, one of which is iontophoresis.

DISCLOSURE OF THE INVENTION

The present invention arises from the discovery that, under specified conditions of applied electrotransport current density (generally expressed in units of microamperes/$cm^2$ herein) and application time, the electrotransport transdermal drug delivery efficiency is enhanced. Electrotransport drug delivery efficiency, E, is defined as the rate of transdermal electrotransport delivery (mg/h) per unit of applied electrotransport current (mA), and expressed in units of milligrams of agent (e.g., drug) delivered per milliamp-hour of applied electric current (mg/mAh). Electrotransport delivery efficiency, in some aspects of its meaning, is analogous to transport number. Transport number is a unitless quantity, less than one, indicating the fractional charge carried by a particular ionic species, e.g., a drug or agent, during electrotransport delivery. Electrotransport delivery efficiency, as defined herein, is more broadly applicable to include the transport of uncharged species and is more reflective of the scope of the invention.

The enhancement of the skin's electrotransport efficiency has been found to be non-transitory, i.e., to last for at least several minutes to several hours or longer after application of this invention. This invention induces (e.g., through a pre-treatment or pre-application step in which species are delivered) a high efficiency drug-transmissive state in the skin to which it is applied. The induced, high efficiency state continues and can be utilized to deliver drug or other therapeutic agent transdermally via electrotransport with increased efficiency. In usual circumstances, this will permit delivery of drug with more precise control and at a lower current. This phenomenon has only been found in the transdermal delivery of drug or agent through intact living skin or tissue, (i.e., in vivo) and is not exhibited in dead skin (i.e., excised skin through which species are electrotransported in vitro).

Generally speaking, this invention involves delivery of a charged species at or above a pre-determined threshold current density $I_c$ for at least a predetermined period of time $t_c$ (e.g., for a predetermined pulse width) through the site of drug delivery, e.g., intact skin. In this manner, the treated skin exhibits a statistically significant, non-transitory increase in drug delivery efficiency relative to skin which has not been so treated. Generally speaking, utilization of this invention will significantly increase the drug/agent delivery efficiency and reduce or eliminate efficiency variability of the skin segment which is so treated. Since electrotransport delivery efficiency remains elevated or less variable after utilization of this invention (relative to untreated skin), utilization of this invention permits the delivery of drug or agent through intact skin by electrotransport with increased control and efficiency.

Briefly, in one aspect, the present invention is a method of electrotransport drug or agent delivery through a body surface involving the steps of:

delivering ionic species by electrotransport at a sufficient current density and over a sufficient period which will change or convert the transport efficiency of the body surface through which the ionic species is delivered to a non-transitory state of higher species delivery efficiency; and thereafter delivering drug or agent through the body surface while in its high efficiency state.

In a preferred practice, current density and species delivery time are selected to maintain the higher efficiency species delivery state of the body surface. This invention also includes the preferred practice of intentionally renewing the highly efficient species delivery state so as to optimize drug delivery efficiency if drug or agent delivery conditions are used which do not periodically renew it. In another preferred practice, the present invention is utilized to deliver drug or agent transdermally, i.e., through intact skin. In yet a further preferred practice, the present invention is used to deliver drug or agent through intact, live, human skin.

In the practice of this invention, the precise current density and treatment time period needed to convert untreated skin to a highly transmissive state have been found to be fairly specific to the drug or therapeutic agent to be delivered. However, for the electrotransport delivery of analgesics, which have been the primary focus of this invention, a treatment of the body site through which drug is to be delivered for a time period of at least 5 msec, and preferably at least 10 msec, at a current density of at least about 40 $\mu A/cm^2$, preferably at least about 50 $\mu A/cm^2$ and most preferably at least about 70 $\mu A/cm^2$ appears to convert the body site so treated to a highly drug transmissive state as defined in this invention. This invention arises because of the discovery that electrotransport delivery efficiency is highly dependent (i.e., it is non-constant) at current densities in the range of about 0 to about 30 $\mu A/cm^2$, is moderately dependent upon current density in the range of about 40 to about 70 $\mu A/cm^2$ and is relatively independent of current density at current densities in excess of about 70 $\mu A/cm^2$.

This unexpected change in efficiency (in theory, efficiency is not predicted to change with increasing current density) permits transdermal electrotransport delivery of drug with significantly enhanced efficiency.

A second unexpected result is achieved in the practice of the present invention, i.e., the change of the skin to the higher efficiency transmissive state is non-transitory with the skin remaining in the higher, and more stable, efficiency state for minutes to hours after the initial transformation, even in cases where the subsequently applied electrotransport current density is lowered to a level below $I_c$ or turned off, completely. In other words, when the skin site has been converted to a highly efficient agent transmissive state by applying a pulsing electric current, the current pulses having a sufficient magnitude to provide a current density at or above the critical current density $I_c$, and preferably over pulse widths of at least 5 msec reduction in applied electrotransport current (and therefore current density) does not cause the skin to immediately return to its initial, lower efficiency state. This observation respecting in vivo drug delivery is critically important to electrotransport system design.

The term "non-transitory" as used herein, when referring to the high efficiency electrotransport agent delivery state, means of sufficient length to permit drug to be delivered to achieve a therapeutic effect. Thus, for example, a relatively inexpensive ionic species may be used to trigger conversion of, e.g., a skin site, to a highly efficient and more stable ionic species delivery state, and thereafter relatively more expensive drug or agent may be delivered at greater efficiency and stability by electrotransport. Where the drug or agent is inexpensive, it may be used to convert the body delivery site to the highly efficient and more stable state, and thereafter may be delivered with greater efficiency, i.e., at lower current density and at greater stability.

The term "high/higher efficiency state" as used herein means conversion of any particular body or skin site to a state in which drug or agent delivery is at least 10% (preferably 20%) more efficient than the same skin site prior to conversion in accordance with this invention. Generally, the parameter which will be most reflective of this efficiency increase is the electrotransport delivery efficiency measured in milligrams of drug delivered per milliamp-hour of applied electrotransport current.

The term "more stable efficiency" as used herein means conversion of a body surface site from a state of more variable electrotransport agent delivery efficiency to one of less variability by exposure of the body site to a current density above the critical current density $I_c$ for a time period longer than the critical time, $t_c$. Critical current density for purposes of increased stability, has been found to be as low as about 40 $\mu A/cm^2$.

In a preferred practice of this invention, it is desirable to be able to change, precisely, drug dosage after the body site has been converted to a highly efficient drug or agent delivery state. In accordance with this invention, total drug or agent delivered (i.e., dosage) may be adjusted while maintaining the required current density to retain the most efficient and stable state, i.e., independent of average current applied by the alternatives of: (a) in a pulsed output electrotransport system, adjustment of device duty cycle while maintaining average current density above the critical current density; (b) in an electrotransport device employing a pulsed output, maintaining constant peak current and pulse width while adjusting pulse frequency to adjust total drug or agent delivered, or (c) the intentional inclusion in and delivery from an "in line" (i.e., to deliver drug) component or subassembly of an electrotransport device of competitive co-ions not having a therapeutic effect converts the system to a stable drug flux at a current density above the critical current density. Delivery of competitive co-ions, for a given current, in addition to the drug or agent ions, provides adequate current density but permits controlled modification of the quantity of therapeutic agent delivered. Delivery of competitive co-ions from, e.g., the drug reservoir, also reduces potentially expensive and potent total drug or agent delivered.

Another way to use an inexpensive ionic species to trigger the skin conversion is to utilize a reverse polarity system. One example of such a system would first drive the anionic drug counter ion from the donor reservoir and the cationic substance from the counter reservoir for the time required to convert the skin to a high efficiency state and then reverses polarity, thereby moving the drug caution into the skin.

In one practice of this invention, the highly potent analgesic drug, fentanyl, is transdermally delivered via electrotransport at very low current density under conditions at which fentanyl delivery tends to be unstable, i.e., to exhibit unacceptable drug delivery efficiency variability. Addition of a chloride salt, e.g., sodium chloride, to the electrode assembly drug reservoir provides sufficient co-deliverable, competitive ion (i.e. $Na^+$) to stabilize fentanyl delivery. In this manner, fentanyl efficiency variability also is reduced or eliminated. These and other aspects of this invention will be discussed below.

BRIEF DESCRIPTION OF THE DRAWINGS

A better understanding of the present invention, as well as other objects and advantages thereof, will become apparent upon consideration of the following modes for carrying out the invention especially when taken with the accompanying drawings, wherein.

MODES FOR CARRYING OUT THE INVENTION

Figure 1:
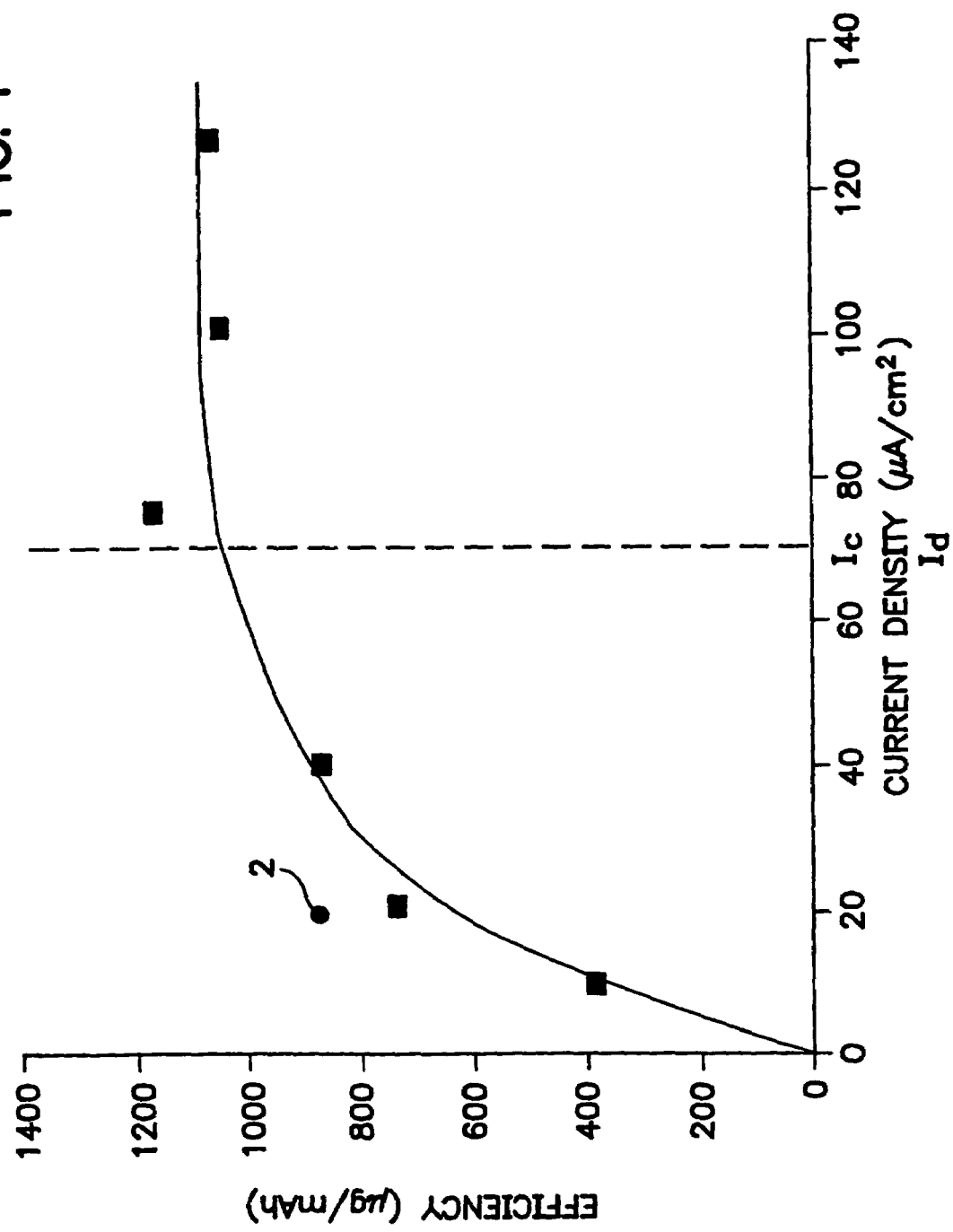
FIG. 1 is a graph of transdermal electrotransport drug delivery efficiency (E) versus applied electrotransport current density (Id for in vivo delivery of fentanyl.

The present invention is based upon the discovery that the efficiency (E) of transdermal electrotransport agent (e.g., drug) delivery is, at least at lower applied electrotransport current densities, dependent on the applied electrotransport current density ($I_d$). This phenomenon is illustrated graphically in FIG. 1. Specifically, we have discovered that when electrotransport current densities at or above a critical current density level, $I_c$, are applied to the skin of living animals for a sufficient period of time, at least as long as a critical period of time $t_c$ on the order of several milliseconds, the electrotransport drug delivery efficiency (E) increases and becomes independent of the level of applied electrotransport current density. It is important to note that the variable electrotransport delivery efficiency effect is a limited exception to the widely reported principle that transdermal electrotransport drug flux is dependent (i.e., linearly dependent) upon the level of applied electrotransport current. Our discovery is that this principle is only true at current densities at or above a critical current density level $I_c$. Thus, we have discovered that, at applied current densities below the critical current density level $I_c$, the rate of electrotransport drug delivery per unit of applied electrotransport current is not constant as has been previously assumed. Not only is the electrotransport drug delivery efficiency (E) variable at lower current densities, it is also lower than at current densities above the critical level $I_c$. Thus, at applied current densities below IC, the electrotransport delivery is less efficient in that more electrotransport current must be applied to deliver a predetermined amount of drug. A still further aspect of our discovery is that the interpatient variability in transdermal electrotransport efficiency is lower at applied current densities above the critical level $I_c$ and higher at applied current density levels below the critical level $I_c$.

In general, the critical current density level $I_c$ for human skin is in the range of about 40 to 100 $\mu A/cm^2$, although the critical level $I_c$ will vary somewhat depending upon (i) the particular drug being delivered, (ii) the particular patient being treated, and (iii) the particular skin location of the patient wearing the electrotransport device. Typically, a current density at or above the critical level $I_c$ need only be applied for several milliseconds to several seconds before the skin enters the high efficiency drug transfer state. However, applied current densities below the critical level $I_c$ are unable to transform the skin into the high efficiency transfer state, even when these low level current densities are applied for extended periods of time (e.g., up to several hours application). This transformation of the skin to a higher efficiency delivery state occurs only in living animals and does not occur with excised skin taken from living or dead animals, i.e., the skin transformation has not been found to occur when in vitro flux studies were run.

Figure 5:
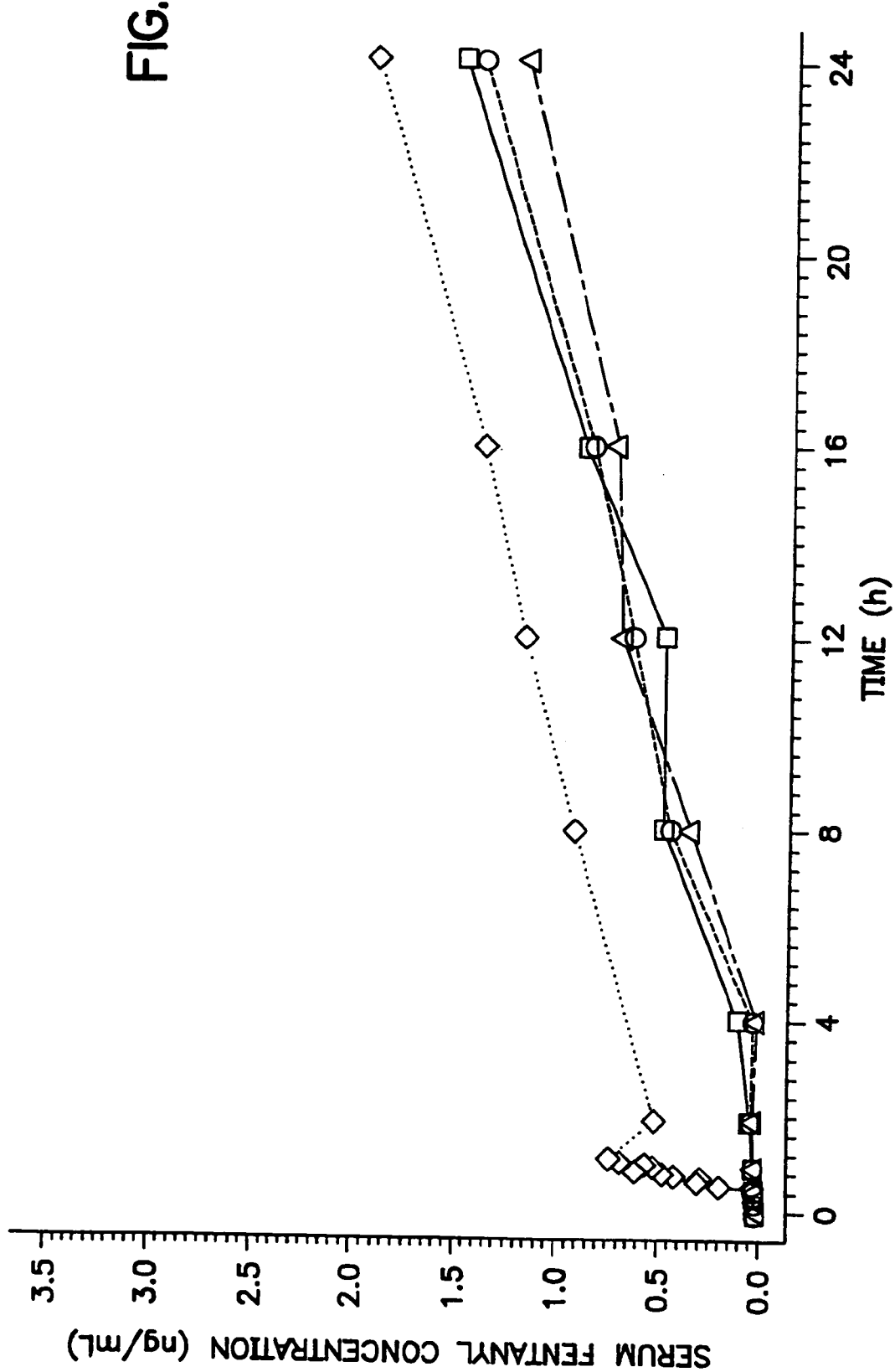
FIG. 5 is a graph of mean serum fentanyl concentration versus time, showing how initial electrotransport administered doses increase subsequent fentanyl delivery through a 24 hour period.

Once the skin has been transformed into the high efficiency transfer state, it tends to remain in that state for an extended period of time (e.g., up to 24 hours) even if no further electrotransport current is thereafter applied to the skin or if only low level current densities (i.e., current densities less than the critical level $I_c$) are thereafter applied to the skin. This result is illustrated in FIG. 5 and is discussed below. The "transformed" skin is in general only those skin sites which are in contact with the donor and counter electrodes/reservoirs of the electrotransport delivery device and through which skin sites the applied current has been passed. Thus, if a skin site on the upper arm of a patient has been transformed by application of electrotransport current densities at or above the critical level $I_c$, the skin on the lower (same) arm, the legs, torso or other arm of the patient does not become transformed. The skin transformation of this invention is a localized phenomenon which is limited to those portions of the skin to which the donor and counter electrodes/reservoirs are attached. Since the skin at the counter electrode site also is converted to the higher efficiency delivery state, methods and devices for delivering agents from the "donor" and "counter" electrodes or both electrodes (e.g., by alternating current polarity) are within the scope of this invention.

Our discovery is particularly critical in those transdermal electrotransport drug delivery regimens wherein the drug is delivered at two (or more) different dosing levels, one dosing level being administered at a current density below the critical level $I_c$ and another dosing level being administered at a current density above the critical level. For example, many drugs are adapted to be administered at a low dose baseline rate for extended periods, the baseline rate being interrupted periodically by periods of higher dosing. Examples of drugs which are administered in this fashion include (1) analgesics, such as fentanyl and sufentanil, which are administered at a low baseline level to treat (e.g., chronic) pain and which are periodically delivered at higher doses to treat more severe episodes of pain; (2) anti-emetics, such as the 5HT3 receptor antagonists ondansetron and granisetron, which are administered continuously at low levels (e.g., during weeks over which a patient is undergoing chemotherapy) and which are periodically administered at higher dosing levels (i.e., during the actual chemotherapeutic administration); (3) anti-epileptics, such as phenytoin, which are delivered continuously at low baseline levels and periodically at higher levels when the patient is undergoing an epileptic seizure; and (4) anti-diabetic drugs, such as insulins, which can be delivered continuously at low baseline levels and periodically (e.g., around meal times) at higher levels. The problem encountered with this type of transdermal electrotransport drug administration is that after the drug is administered at the higher dosing rate (with the applied current density above the critical level, $I_c$), when the applied electrotransport current is readjusted to apply the original lower baseline level, the transdermal electrotransport drug flux does not return to the same baseline level. The drug flux instead falls to a level somewhere between the original baseline rate and the high dosing rate, because the skin has been transformed into a higher efficiency drug delivery state. For example, if the efficiency is enhanced by a factor of two, after the skin has experienced a current density above the critical current density, and then the current is lowered to the original baseline current, the drug delivery rate would be twice that experienced before the transformation. The higher baseline rate could result in a drug overdose if the electrotransport system does not compensate for this shift in efficiency. To eliminate this problem, the electrotransport system should reduce the current applied (e.g., by approximately a factor of two) after the skin has experienced a current density greater than $I_c$. With reference to FIG. 1, data point 2 is a likely efficiency that would be experienced at the drug delivery site were current (and therefore current density) reduced after exposure of the body site to a current density at or above $I_c$ for at least a period of time $t_c$. At data point "2", the electrotransport agent delivery efficiency is higher than the agent delivery efficiency which was experienced initially (i.e., before exposure to a current density above $I_c$) at the current density of 20 $\mu A/cm^2$.

A more elegant approach to this problem is to apply a pulsed electrotransport current to the skin, the pulsing current having a magnitude above the critical level $I_c$, and to modify the duty cycle of the pulses to increase or decrease the amount of drug delivered. The term "duty cycle" as used herein is the ratio of "on" time interval to the period of time of one cycle (i.e., the ratio of the pulse-duration time to the pulse-period) and is usually expressed as a percent. For example, if a device is "on" for 500 ms of a 1 sec cycle, then the device is operating in a 50% duty cycle. In this practice of the invention, the magnitude of the current pulses is selected in view of the known area of the surface from which drug is delivered, thereby defining a fixed and known current density (i.e., the ratio of current to the area from which current flows). Thus, if it is decided, based upon application of the above principles, that a specific maximum current for a given anode surface area e.g., $I_{max}$, will provide the enhanced efficiency drug delivery discussed above, then by increasing or decreasing the duty cycle, the amount of drug delivered at the high efficiency state can be increased or decreased without causing the applied current density to change. In choosing the parameters of drug delivery if using this approach, the magnitude of the current pulses is selected so that the resulting current density transforms the skin into the high efficiency state and the duty cycle of the current pulses is altered to adjust the drug delivery rate (i.e., a low dose of drug is administered by a high density (i.e., greater than or equal to $I_c$) pulsing current having a low duty cycle and a high dose of drug is administered by the same magnitude current density but being pulsed at a longer pulse width corresponding to a higher duty cycle.

Figure 2:
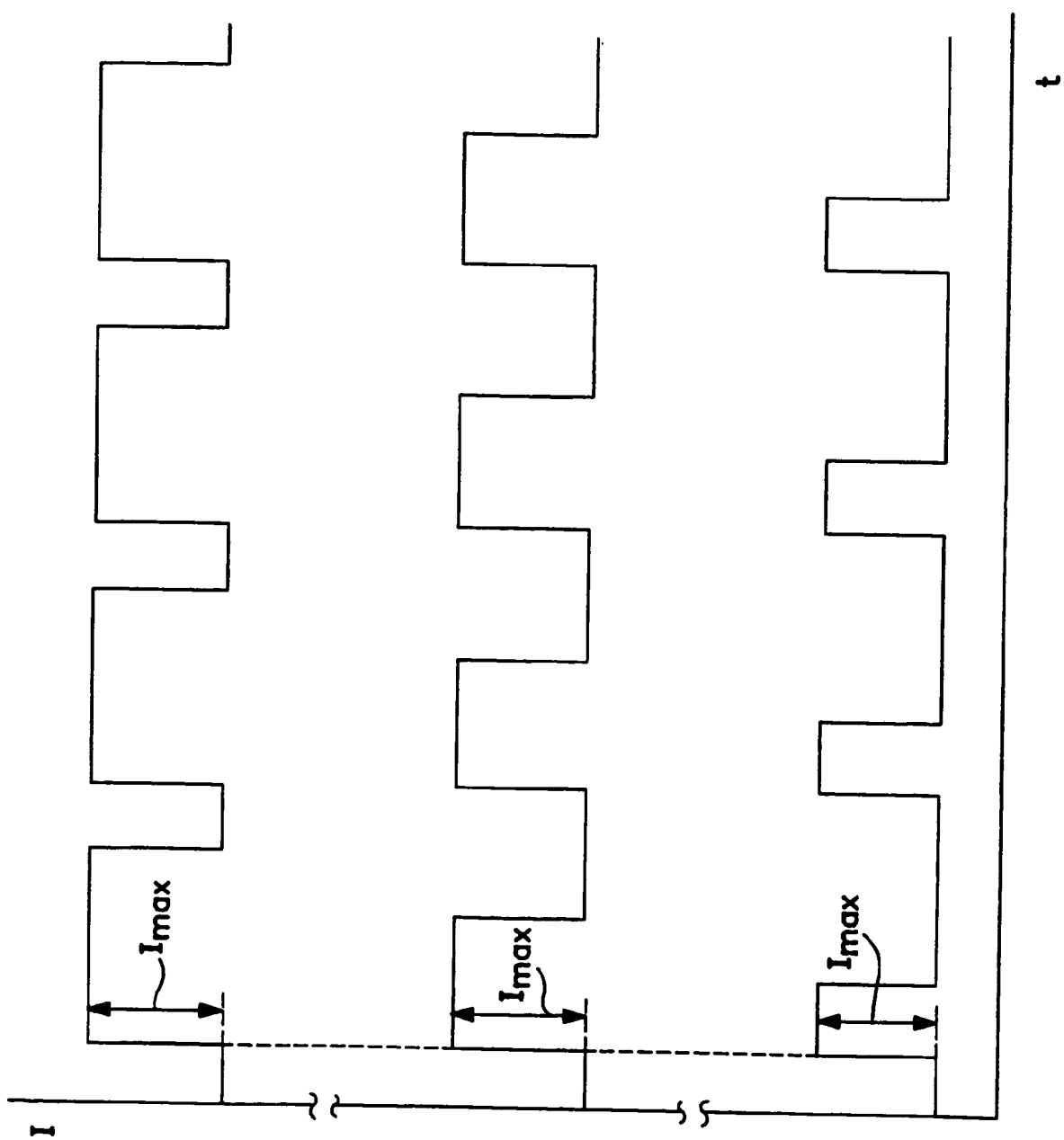
FIG. 2 is a graph of electrotransport current versus time, showing three pulsed current waveforms having differing duty cycles.

This aspect of the invention is more specifically illustrated in FIG. 2 where waveforms for three different pulsing electrotransport currents of the same frequency are shown. In FIG. 2 time is illustrated on the horizontal axis, while current amplitude is illustrated on the vertical axis. The three current waveforms shown in FIG. 2 all have the same magnitude, and hence the same maximum applied current density $I_{max}$ for an electrotransport delivery device of any one size. This particular current density $I_{max}$, is greater than the critical current density level $I_c$. The three current waveforms have differing duty cycles, which is the percentage of time during which the current is applied. The three waveforms have duty cycles of 75% (top waveform), 50% (middle waveform) and 25% (bottom waveform). Thus, the 25% duty cycle waveform delivers drug transdermally by electrotransport at about one-half the dosing level of the 50% duty cycle waveform and about one-third the dosing level of the 75% duty cycle waveform. All three waveforms administer drug transdermally by electrotransport through skin which is transformed into the high efficiency transfer state by reason of $I_{max}$ being greater than $I_c$.

Figure 4:
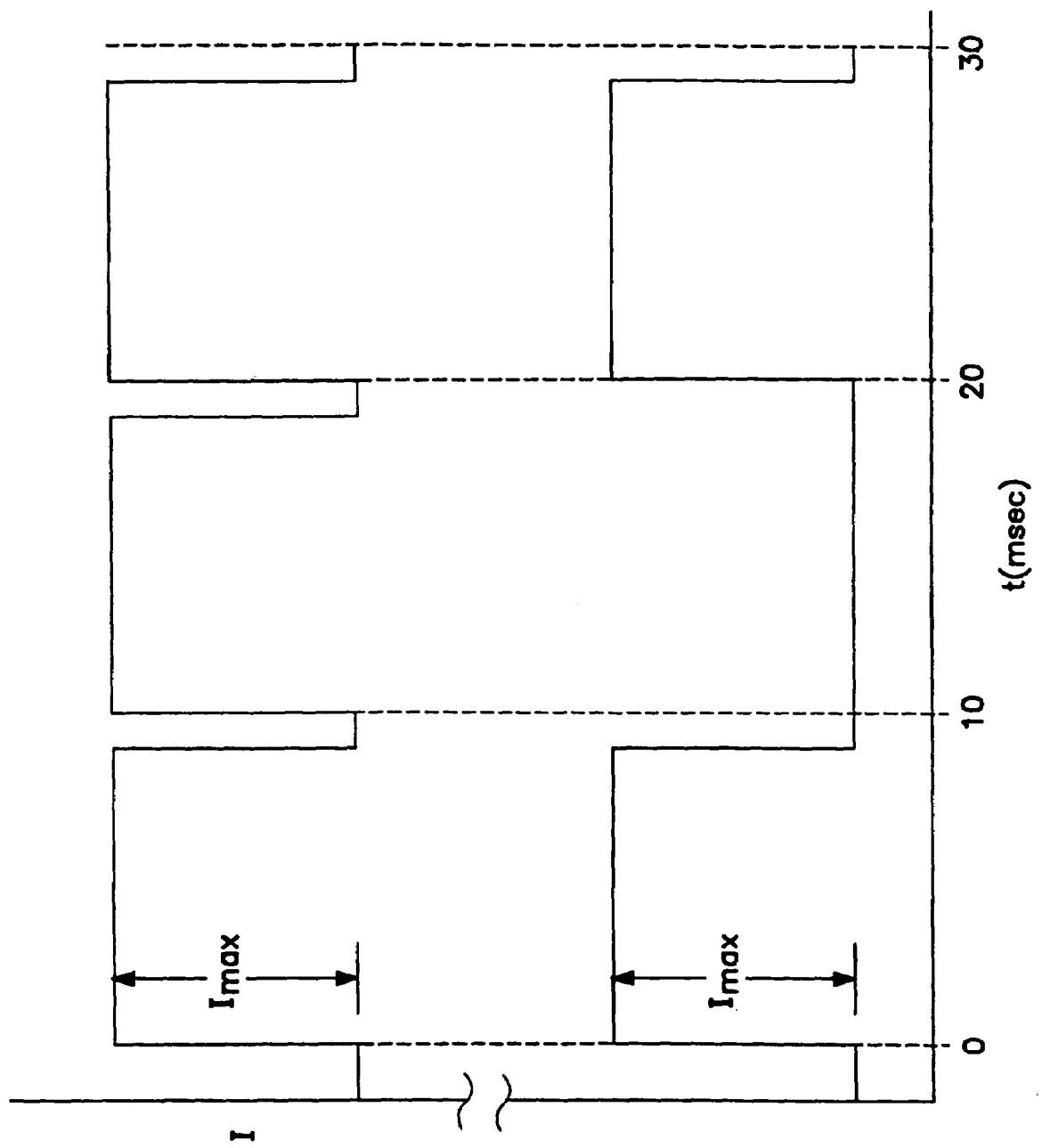
FIG. 4 is a graph of electrotransport current versus time, showing two pulsed current waveforms having the same peak current and pulse width but different pulsing frequencies.

In a further practice of this invention, the pulsing frequency of a pulsed current waveform is adjusted to control the overall quantity of drug delivered while holding the pulse width constant and maintaining the magnitude of current pulses at or above $I_c$. In this manner, current density is maintained at or above the level which transforms the skin into the high efficiency state. Exemplary of this, a device employing a pulsed current waveform having current pulses with a magnitude of 0.2 mA, a pulse width of 10 msec, and a frequency of 10 Hz will deliver roughly half as much drug as the same device run at a frequency of 20 Hz. Given a constant drug delivery area, e.g., of an electrode assembly, the applied current densities of these two devices is the same and is above the high efficiency critical level $I_c$ so that both devices deliver drug transdermally by electrotransport with higher efficiency and lower variability compared to devices which apply electrotransport current at current densities below the critical level $I_c$. From these two examples of the invention, one skilled in this art will appreciate that a combination of frequency and duty cycle may be used to alter the rate of drug delivery while maintaining the maximum applied current density, $I_{max}$, above $I_c$. FIG. 4 shows the waveforms for a device operated to have a constant 9 msec pulse width, the frequency for a device operated according to the lower waveform being one-half that of a device operated according to the upper waveform (i.e., 50 Hz versus 100 Hz).

As is noted above, agent delivery efficiency is increased by exposure of the site to a current density at or above $I_c$ and for a time period equal to or greater than a critical time, $t_c$. Generally speaking, for a pulsing electrotransport device, the pulse width must equal or exceed $t_c$. Thus, $t_c$, in a practice of this invention using pulsed current electrotransport devices and for delivery of fentanyl, falls between about 0.5 msec and 30 msec. It is believed that the minimum pulse width to cause transformation to the higher efficiency state is about 10 msec for fentanyl.

Table 1 shows data which support the above observation. Table 1 shows drug delivery efficiency data for a device programmed to run at frequencies of 1 Hz, 10 Hz and 625 Hz. A 31% duty cycle was employed.

TABLE 1

| | | Rate of Fentanyl Delivery µg/hr. | |
|---|---|---|---|
| Frequency Hz | Pulse Width | Without Bolus Treatment | After Bolus Treatment* |
| 625 | 0.5 msec | 7 | 34 |
| 10 | 31 msec | 52** | 52** |
| 1 | 310 msec | 48** | 48** |

*"Bolus Treatment" means a direct current bolus delivery of fentanyl for a period of 30 minutes at a current density of 0.1 mA/cm².
**The numbers in these two columns are the same because even at a pulse width as short as 31 msec, the skin site had already transformed to its highly efficient state.

Table 1 also indicates that fentanyl delivery is significantly lower at a high pulsing frequency of 625 Hz compared to the lower pulsing frequencies of 1 and 10 Hz. This phenomenon is called capacitive loss, which loss becomes greater as pulsing frequency is increased at a given duty cycle. Capacitive loss results because a portion of each pulse is consumed by the process of charging the skin without delivering drug. The shorter the pulse width (and hence the higher the pulsing frequency), the greater (relatively speaking) the capacitive loss for each pulse. Table 1 also shows that until a critical pulse width is achieved, regardless of frequency, no transformation of the body site agent delivery efficiency occurs.

Pulsed current electrotransport devices are well known in the art. Such devices are described in numerous technical articles and the patent literature including Bagniefski et al. "A Comparison of Pulsed and Continuous Current Iontophoresis", *Journal of Controlled Release,* 113–122, (1090); McNichols et al., U.S. Pat. No. 5,047,007; Sibalis U.S. Pat. No. 5,135,478; R. Burnette et al. "Influence of Constant Current Iontophoresis on the Impedance and Passive Na$^+$ Permeability of Excised Nude Mouse Skin", 77 *J. Pharmaceutical Sciences* 492 (1988); Pikal et al, "Study of the Mechanisms of Flux Enhancement Through Hairless Mouse Skin by Pulsed DC Iontophoresis," 8 *Pharmaceutical Research* 365 (1991).

Another method of transdermally delivering a therapeutic agent (e.g., a drug) by electrotransport at an applied current density at or above the critical level $I_c$ but at a lower dosing/delivery rate (i.e., a rate which requires a current lower than that achieved when applying a current sufficient to achieve a current density of at least $I_c$) involves the intentional introduction of competitive ions having the same (i.e., same polarity) charge as the therapeutic agent ions. This approach, under the specific conditions described, permits drug dosage control as well as providing enhanced stability and enhanced efficiency of electrotransport of therapeutic agent. This approach is generally discouraged in the patent literature because it otherwise tends to reduce drug delivery efficiency. This aspect of this invention is particularly applicable to electrotransport delivery of those drugs or therapeutic agents which are therapeutically effective when (i) delivered at low transdermal fluxes and/or (ii) when present in low concentrations in the blood. Generally speaking, this aspect of the present invention is particularly applicable to the electrotransport delivery of highly potent drugs or other therapeutic agents.

The competitive ionic species can be loaded into the donor reservoir (e.g., a biocompatible salt is added to the donor reservoir) before electrotransport agent delivery and/or can be generated in situ during the operation of the electrotransport device. Generation of competitive ionic species in situ may be accomplished using a secondary electrode and appropriate electrical control circuitry as described in Phipps et al U.S. Pat. No. 5,443,442 for example.

The amount of the competitive species intentionally added to the donor reservoir will be specific to the drug or agents to be delivered and the relative electrophoretic mobilities of the drug ions and the competing ionic species. Generally, the competitive species will be ionic and should have delivery characteristics similar to those of the drug being delivered. The quantity of delivered species to be added is selected so that the total current density is raised above the critical current density, $I_c$, where the ionic species efficiency is normalized or stabilized so that variation of delivery efficiency is no longer experienced.

The teachings in Theeuwes et al. U.S. Pat. No. 5,080,646 may be utilized in determining the proper amount of competitive co-ion species to be added to the donor reservoir of an electrotransport delivery device. The patent discusses the processes involved in the transport of species through a biological surface such as skin, mucosa, or tissue. The Theeuwes et al patent provides a mathematical analysis which permits one skilled in this art, when unacceptable random variability of electrically-assisted drug flux is experienced, to select a suitable quantity and species of competetive co-ion to be delivered along with the drug or agent.

The transdermal electrotransport drug delivery efficiency may be increased, when using a pulsing electrotransport current, by maintaining the pulse width equal to or greater than $t_c$. In general, this requires the pulsing frequency to be maintained below about 100 Hz, and preferably less than about 10 Hz. The term "pulsing electrotransport current" as used herein means a current which varies in a periodic fashion. A pulsing electrotransport current which transforms the skin to the high efficiency transfer state is one where at least a portion of the periodic current waveform provides a current density below $I_c$, and another portion which has a sufficient magnitude and pulse width to effect transformation of the skin to the higher efficiency drug delivery state. This then provides the second of the two necessary and sufficient parameters (after current density $I_c$) which must be satisfied to apply this invention. As was noted above, pulsing frequencies in the relatively low ranges discussed here combined with sufficient duty cycle, provide the pulse width needed for in vivo skin drug delivery efficiency to increase. For example, a frequency of about 10 Hz (i.e., a period of about 100 msec) and a duty cycle of 31% was found to provide a pulse width of 31 msec which was long enough to induce a skin efficiency increase to deliver fentanyl at a current density of 0.1 mA/cm$^2$.

Figure 3:
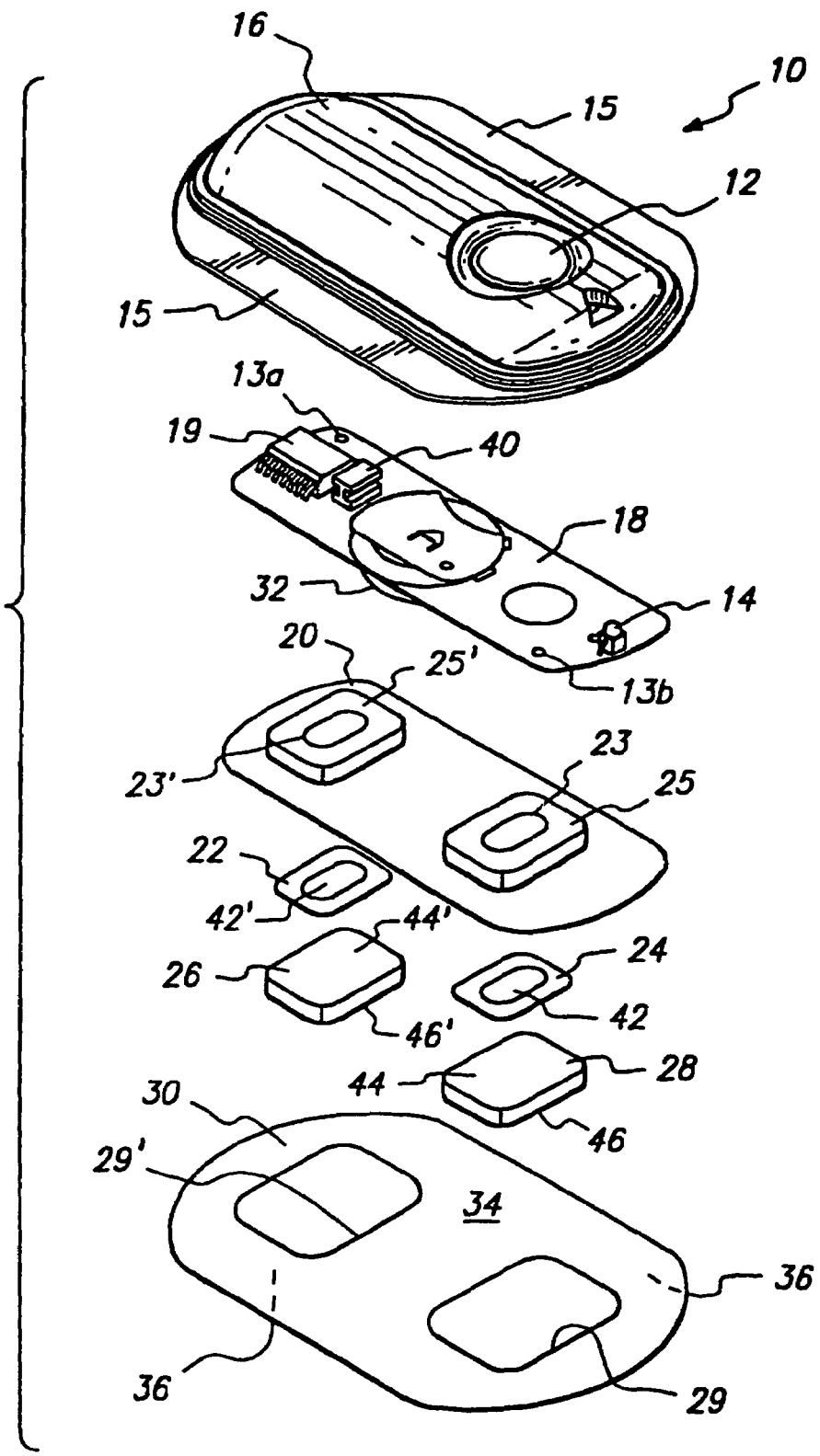
FIG. 3 is an exploded perspective view of a transdermal electrotransport drug delivery device which can be used in accordance with the method of the present invention.

Reference is now made to FIG. 3 which depicts an exemplary electrotransport device which can be used in accordance with the present invention. FIG. 3 shows a perspective exploded view of an electrotransport device 10 having an activation switch in the form of a push button switch 12 and a display in the form of a light emitting diode (LED) 14. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete electrical components 40 and battery 32. Circuit board assembly 18 is attached to housing 16 by posts (not shown in FIG. 3) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a battery 32, which is preferably a button cell battery and most preferably a lithium cell. Other types of batteries, such as sizes AAA and AAAA, may also be employed to power device 10.

The circuit outputs (not shown in FIG. 3) of the circuit board assembly 18 make electrical contact with the electrodes 24 and 22 through openings 23,23' in the depressions 25,25' formed in lower housing, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30. Upon depression of push button switch 12, the electronic circuitry on circuit board assembly 18 delivers a predetermined DC current to the electrodes/reservoirs 22,26 and 24,28 for a delivery interval of predetermined length, e.g., about 10 minutes. Preferably, the device transmits to the user a visual and/or audible confirmation of the onset of the drug delivery, or bolus, interval by means of LED 14 becoming lit and/or an audible sound signal from, e.g., a "beeper". Drug (e.g., an analgesic drug such as fentanyl) is then delivered through the patient's skin, e.g., on the arm, for the predetermined (e.g., 10 minute) delivery interval. In practice, a user receives feedback as to the onset of the drug delivery interval by visual (LED 14 becomes lit) and/or audible signals (a beep from the "beeper"). A preferred device is described in commonly owned, pending patent application entitled "Display for an Electrotransport Device", U.S. patent application Ser. No. 08/410,112, filed Mar. 24, 1995.

Anodic electrode 22 is preferably comprised of silver and cathodic electrode 24 is preferably comprised of silver chloride. Both reservoirs 26 and 28 are preferably comprised of polymer hydrogel materials as described herein. Electrodes 22, 24 and reservoirs 26, 28 are retained by lower housing 20. When the drug being delivered by electrotransport is cationic, the anodic reservoir 26 is the "donor" reservoir which contains the drug and the cathodic reservoir 28 contains a biocompatible electrolyte. When the drug being delivered by electrotransport is anionic, the cathodic reservoir 28 is the "donor" reservoir which contains the drug and the anodic reservoir 26 contains a biocompatible electrolyte.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body thereby allowing freedom of movement at, and around, the wearing site. The anode/drug reservoir 26 and the cathode/salt reservoir 28 are located on the skin-contacting side of device 10 and are sufficiently separated to prevent accidental electrical shorting during normal handling and use.

The device 10 adheres to the patients body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depressions 25,25' as well as retains lower housing 20 attached to upper housing 16.

The push button switch 12 is located on the top side of device 10 and is easily actuated through clothing. A double press of the push button switch 12 within a short period of time, e.g., three seconds, is preferably used to activate the device 10 for delivery of drug, thereby minimizing the likelihood of inadvertent actuation of the device 10.

Upon switch activation an audible alarm signals the start of drug delivery, at which time the circuit supplies a predetermined level of DC current to the electrodes/reservoirs for a predetermined (e.g., 10 minute) delivery interval. The LED 14 remains "on" throughout the delivery interval indicating that the device 10 is in an active drug delivery mode. The battery preferably has sufficient capacity to continuously power the device 10 at the predetermined level of DC current for the entire (e.g., 24 hour) wearing period.

The present invention is particularly useful in the transformation of human skin in the transdermal electrotransport delivery of drugs to humans. However, the invention also has utility in delivering drugs to other animals and is not limited to humans.

The terms "agent" and "drug" are used interchangeably herein and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics including gastrointestinal and urinary antspasmodics, anticholinergics, sympathomimetrics, xanthine derivatives, cardiovascular preparations including calcium channel blockers, beta-blockers, antiarrythmics, antihypertensives, diuretics, vasodilators including general, coronary, peripheral and cerebral vasodilators, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

The present invention can be used to deliver transdermally by electrotransport the following drugs: interferons, alfentanyl, amphotericin B, angiopeptin, baclofen, beclomethasone, betamethasone, bisphosphonates, bromocriptine, buserelin, buspirone, calcitonin, ciclopirox, olamine, copper, cromolyn sodium, desmopressin, diclofenac diflorasone, diltiazem, dobutamine, dopamine agonists, dopamine agonists, doxazosin, droperidol, enalapril, enalaprilat, fentanyl, encainide, G-CSF, GM-CSF, M-CSF, GHRF, GHRH, gonadorelin, goserelin, granisetron, haloperidol, hydrocortisone, indomethacin, insulin, insulinotropin, interleukins, isosorbide dinitrate, ketoprofen, ketorolac, leuprolide, LHRH, lidocaine, lisinopril, LMW heparin, melatonin, methotrexate, metoclopramide, miconazole, midazolam, nafarelin, nicardipine, NMDA antagonists, octreotide, ondansetron, oxybutynin, $PGE_1$, piroxicam, pramipexole, prazosin, prednisolone, prostaglandins, scopolamine, seglitide, sufentanil, terbutaline, testosterone, tetracaine, tropisetron, vapreotide, vasopressin, verapamil, warfarin, zacopride, zinc, and zotasetron.

This invention is also believed to be useful in the transdermal electrotransport delivery of peptides, polypeptides and other macromolecules typically having a molecular weight of at least about 300 daltons, and typically a molecular weight in the range of about 300 to 40,000 daltons. Specific examples of peptides and proteins in this size range include, without limitation, LHRH, LHRH analogs such as buserelin, gonadorelin, nafarelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc,), follicle luteoids, αANF, growth hormone releasing factor (GHRF), βMSH, TGF-β, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulogs, hyaluronidase, interferons, insulin-like growth factors, interleukins, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, opiate peptides, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant).

Generally speaking, it is most preferable to use a water soluble form of the drug or agent to be delivered. Drug or agent precursors, i.e., species which generate the selected species by physical or chemical processes such as ionization, dissociation, dissolution or covalent chemical modification (i.e., prodrugs), are within the definition of "agent" or "drug" herein. "Drug" or "agent" is to be understood to include charged and uncharged species as described above.

While the disclosure has focussed upon the electrotransport delivery of ionic species, the present invention is also applicable to the electrotransport delivery of uncharged species, e.g., by electroosmosis. Thus, the transformation of the skin into the high efficiency transport state is not limited to electrically assisted transport of ionic species but also to electroosmotic delivery of uncharged (i.e., non-ionized) species.

The following examples illustrate some of the advantages of the present invention.

EXAMPLE 1

Current Density and Increased Efficiency

This study evaluated the effect of applied current on electrotransport drug delivery efficiency. Drug delivery efficiency is expressed in terms of the rate of drug delivery per unit of applied current. The study involved the application of electrotransport devices to eighteen healthy male volunteers for a duration of about one day.

The two electrotransport treatments involved the delivery of fentanyl from a donor reservoir containing an aqueous solution of fentanyl HCl and having a skin contact area of 5 $cm^2$, at a baseline current of 100 µA. Thus, the applied electrotransport current density was 20 $\mu A/cm^2$ (=100 µA 5 $cm^2$). Six of the eighteen volunteers were administered 4 bolus doses during the first hour of treatment by applying current levels of 1300 µA (i.e., an applied electrotransport current density of 260 $\mu A/cm^2$) for a duration of 2.5 minutes at 15 minute intervals. Following the administration of the four boluses in the first hour of treatment, these six volunteers received continuous transdermal electrotransport fentanyl administration at a current density of 20 $\mu A/cm^2$ from hour 2 through 24 hours. The remaining twelve volunteers received continuous transdermal electrotransport fentanyl administration at a current density of 20 $\mu A/cm^2$ over the entire 24 hour delivery period. After the treatment period, the electrotransport devices were removed. The skin site was then washed to remove any residual fentanyl.

Blood samples were taken over the entire 24 hour period commencing with the application of current from the electrotransport devices. Serum fentanyl concentrations were used to calculate mean transdermal fentanyl fluxes using subject specific pharmacokinetic parameters and conventional methods.

FIG. 5 shows that once a skin site receives a minimum level of current (for a fixed electrode area) for a sufficient duration, a high electrotransport efficiency state is achieved. FIG. 5 shows the mean serum fentanyl concentration in the blood of the subjects over the 24 hour testing period. As is shown in the uppermost curve (◊ ... ◊ ... ◊) in FIG. 5, the six volunteers which received the four 260 $\mu A/cm^2$, 2.5 minute bolus administrations in the first hour exhibited higher efficiency fentanyl transdermal delivery than the group of twelve subjects shown as three groups of four in the three lower curves (to emphasize inherent variability) who received only the 20 $\mu A/cm^2$ constant DC current. Once this high-efficiency transport state is achieved, more drug is delivered through the skin per unit of applied current. Further, the effect lasted the entire 24 hours of the treatment. This is indicated by the vertical separation between the upper curve and the three lower curves in FIG. 5.

Specifically, the six volunteers who received the four 260 $\mu A/cm^2$ doses in the first hour of treatment exhibited a mean transdermal fentanyl flux of 113 µg/h while the twelve volunteers who received only the 20 $\mu A/cm^2$ baseline current exhibited a mean transdermal fentanyl flux of 57 µg/h. This indicates that the efficiency was enhanced by about a factor of two as a result of the initial high current density boluses.

EXAMPLE 2

Current Density and Fentanyl Flux

This study was undertaken to evaluate the relationship of current density and drug flux in the transdermal electrotansport delivery of fentanyl. Electrotransport devices, delivering constant DC currents, were applied to 8 healthy male volunteers for a duration of 24 hours. The three electrotransport treatment regimens in this study differed only in the applied electrotransport current (and therefore current density) levels. The electrotransport devices delivered fentanyl through the skin from a donor hydrogel having a skin contact surface area of 5 $cm^2$. The gels were imbibed with an aqueous solution of fentanyl HCl. The current density levels used in this study were 10, 20, and 40 $\mu A/cm^2$. After a 24 hour treatment period, the electrotransport devices were removed. The skin site was then washed to remove any residual fentanyl. All 8 volunteers received each treatment approximately 1 week apart.

Figure 6:
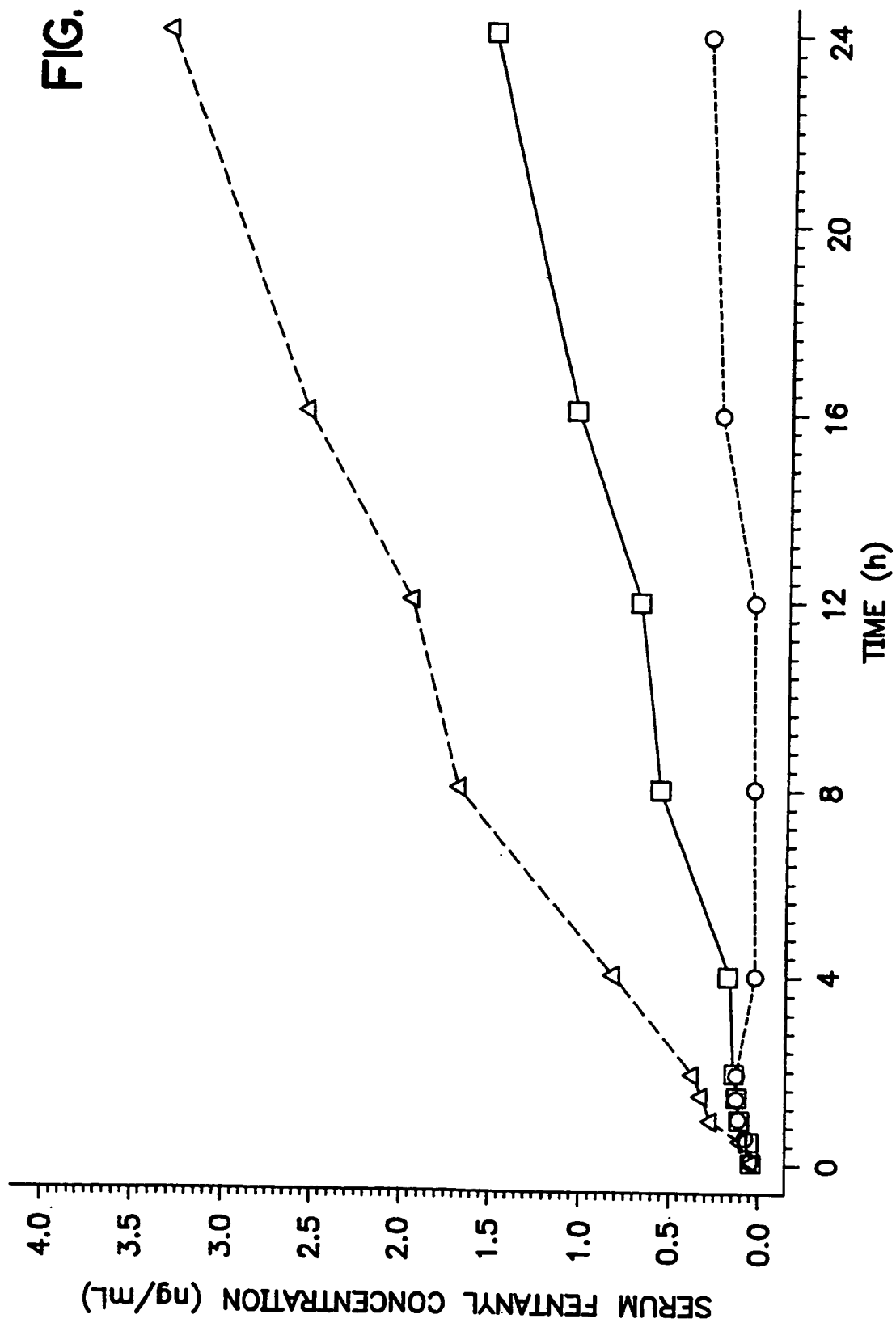
FIG. 6 is a graph of average serum fentanyl concentration, as a function of time, for applied electrotransport current densities of 10, 20 and 40 $\mu A/cm^2$.

For each treatment, blood samples were taken over a 24 hour period commencing with the application of current from the electrotransport devices. Serum fentanyl concentrations over the first 24 hours are shown in FIG. 6. The top curve (-Δ-Δ-Δ-) in FIG. 6 was the 200 µA treatment (i.e., 40 $\mu A/cm^2$), the middle curve (-□-□-□-) the 100 µA treatment (i.e., 20 $\mu A/cm^2$) and the bottom curve (-0-0-0-) the 50 µA treatment (i.e., 10 $\mu A/cm^2$). As in Example 1, the serum fentanyl concentrations from each patient were used to calculate mean drug rate and the mean total amount of drug delivered. A drug delivery efficiency level for each treatment was derived by dividing the mean fentanyl rate by the current density applied to the skin.

The average transdermal fentanyl rates were 19, 73 and 173 µg/h at the applied current densities 10, 20 and 40 $\mu A/cm^2$, respectively. This data shows a non-linear relationship between applied current and transdermal electrotransport drug flux within the electrotransport current density range of 10 to 40 $\mu A/cm^2$. An almost ten-fold increase in drug rate was observed as the current was increased four-fold from 50 µA to 200 µA. This unexpected result indicates that the efficiency of fentanyl delivery was enhanced by a factor of about 2.5-fold due to the change in current density from 10 to 40 $\mu A/cm^2$.

EXAMPLE 3

This study was undertaken to evaluate the relationship between current density and drug flux in the transdermal electrotransport delivery of goserelin. The study involved the application of electrotransport devices, applying constant current, to 12 normal male volunteers for a duration of 8 hours.

The two electrotransport treatment regimens in this study differed only in applied current density levels. The electrotransport devices delivered goserelin through the skin from polyvinyl alcohol (PVOH)-based donor hydrogels having a skin-contact surface area of 4 cm². The gels contained an aqueous goserelin solution. The current density levels used in this study were 50 and 100 µA/cm². After an 8 hour treatment period, the electrotransport devices were removed. The skin site was then washed to remove any residual goserelin. All 12 volunteers received each treatment seven days apart.

For each treatment, seven blood samples were taken over a 24 hour period commencing with the application of current from the electrotransport devices. Serum goserelin concentrations from each patient were used to calculate mean drug flux and the mean total amount of drug delivered.

Figure 8:
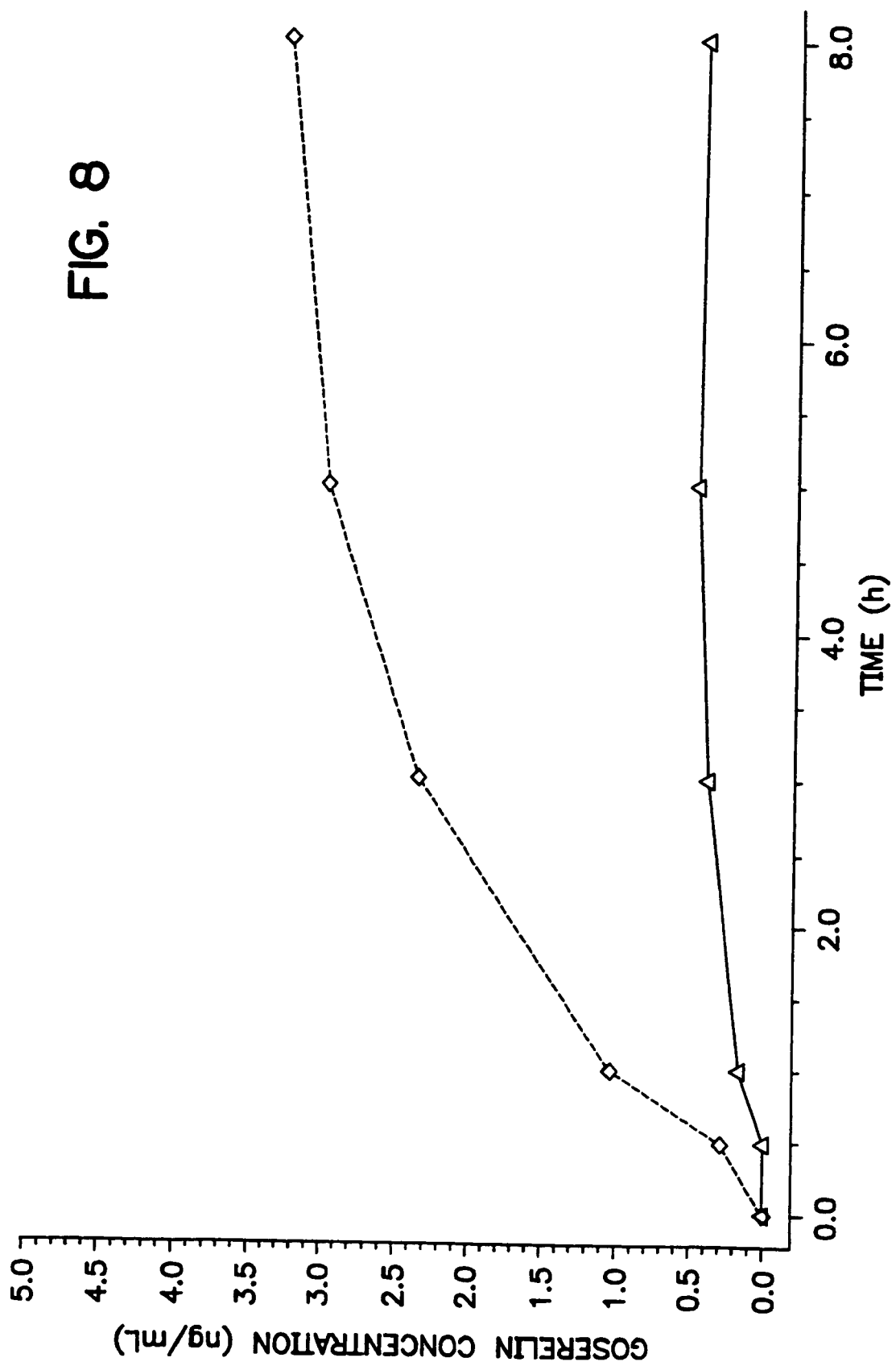
FIG. 8 is a graph of serum goserelin concentration versus time, for applied electrotransport current densities of 50 and 100 $\mu A/cm^2$.

FIG. 8 shows the goserelin blood plasma concentrations for the 8 hour duration of electrotransport administration for the two current densities (i.e., 50 and 100 µA/cm²). The 100 µA/cm² curve is the upper curve in FIG. 8 while the lower curve in FIG. 8 is the 50 µA/cm² data. From this concentration data, transdermal goserelin fluxes were calculated. The average transdermal goserelin flux was 5.8 µg/h at an applied current density of 50 µA/cm² while the average transdermal flux of goserelin was 21.6 µg/h at an applied current density of 100 µA/cm². Thus, a non-linear relationship between applied current density and drug flux was shown by the data. An almost fourfold increase in drug flux is observed as the current density rises from 50 to 100 µA/cm². This data also suggests the existence of a critical current density, $I_c$, which for transdermal electrotransport delivery of goserelin falls between 50 and 100 µA/cm², above which more drug is delivered through the skin per unit of applied current. The remaining example utilizes a pulsing electrotransport current, and is therefore relevant only to a preferred aspect of the present invention wherein the applied electrotransport current is a pulsing current with current pulses having a pulse width of at least 5 msec, and more preferably a pulse width of at least 10 msec.

EXAMPLE 4

Pulsing Frequency and Fentanyl Flux

This study assessed the effect of pulsing frequency on the electrotransport delivery of fentanyl using pulsed current waveforms. The frequencies evaluated in this study were 1, 10, and 625 Hz.

The electrotransport devices were configured to deliver a 200 µA square wave current pulse, having a 31% duty cycle. The electrotransport devices delivered fentanyl through the skin from a donor hydrogel having a skin contact surface area of 2 cm². Thus, during the applied electrotransport current pulses, the current density was 100 µA/cm² (=200 µA÷2 cm²). The gels were imbibed with an aqueous solution of fentanyl HCl. After treatment periods of varying duration, the electrotransport devices were removed. The skin site was then washed to remove any residual fentanyl.

For each treatment, blood samples were taken commencing with the application of current from the electrotransport devices. Serum fentanyl levels from each patient were used to calculate mean drug flux.

Figure 7:
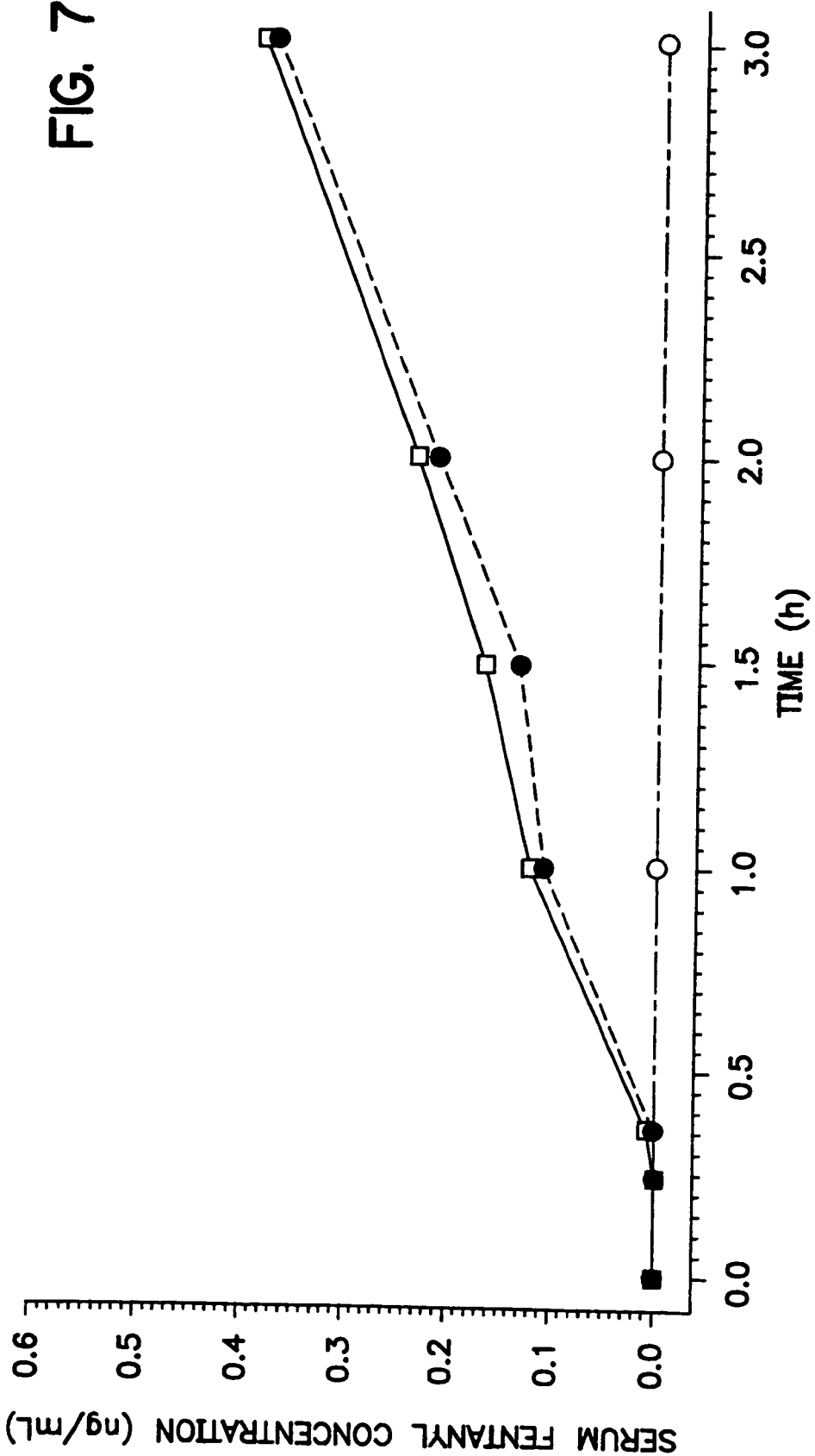
FIG. 7 is a graph of serum fentanyl concentration versus time for delivery of fentanyl at pulsing frequencies of 1, 10, and 625 Hz.

FIG. 7 shows that the use of a square-wave frequency of 625 Hz resulted in minimal fentanyl flux. This is shown in the lower most nearly horizontal curve in FIG. 7. The use of the lower pulsing frequencies, 1 and 10 Hz, resulted in increased fentanyl flux. This is shown in the upper two curves of FIG. 7. No statistically significant difference in fentanyl flux was observed between 1 and 10 Hz. These results suggest that the use of lower pulsing frequencies results in higher electrotransport delivery efficiency of fentanyl.

The above disclosure will suggest many alternatives, permutations, and variations of the invention to one skilled in this art without departing from the scope of the invention. The above disclosure is intended to be illustrative and not exhaustive. All such, permutations, variations, and alternatives suggested by the above disclosure are to be included within the scope of the attached claims.

We claim:

1. An electrotransport device for in vivo delivery of a charged agent through a body at surface at a higher electrotransport agent delivery efficiency (E) defined by the agent delivery rate per unit of applied current; the device (10) having a donor reservoir (26, 46) containing the charged agent and having a delivery area, and having a source of electrical power (32) and a current controller (19, 40), the device (10) being characterized by:
   the current controller (19, 40) being adapted to provide an applied pulsing DC current having a periodic current waveform, a pulsing frequency, and a duty cycle, the pulsing current applied to the reservoir (26, 46) and to the body surface, wherein an applied current density is defined by the applied pulsing current divided by the delivery area, and wherein a higher electrotransport agent delivery efficiency (E) state is induced in the body surface when the applied current density is greater than or equal to a critical current density level ($I_c$) and the applied pulsing current is applied for greater than or equal to a critical time period ($t_c$).

2. The device of claim 1, wherein the agent delivery efficiency (E) is more stable when the applied current density is above the critical level ($I_c$) and less stable when the applied current density is below the critical level ($I_c$).

3. The device of claim 1, wherein the device (10) is adapted to be applied to intact human skin and the controller (19, 40) is adapted to provide an applied current density of at least about 40 µA/cm².

4. The device of claim 1, wherein the agent is fentanyl and the controller (19, 40) is adapted to provide an applied current density of at least about 40 µA/cm² for at least about 10 msec.

5. The device of claim 1, wherein the agent is goserelin and the controller (19, 40) is adapted to vary and control the periodic current waveform to provide an applied current density of at least about 50 µA/cm² for at least about 10 msec.

6. The device of claim 1, wherein $t_c$ is at least 5 msec.

7. The device of claim 1, wherein the periodic current waveform has a current magnitude that provides a second applied current density less than $I_c$.

8. The device of claim 7, wherein the second applied current density is approximately zero.

9. The device of claim 7, wherein the controller (19, 40) is adapted to vary the duty cycle and the agent delivery rate.

10. The device of claim 7, wherein the controller (19, 40) is adapted to vary the frequency and the agent delivery rate.

11. The device of claim 1, wherein the donor reservoir contains at least one suitable competitive specie.

12. The device of claim 1, wherein the controller (19, 40) is adapted to vary and control the frequency of the applied pulsing current to less than about 100 Hz.

13. The device of claim 1, wherein the controller (19, 40) is adapted to vary and control the frequency of the applied pulsing current to less than about 10 Hz.

14. A method of in vivo delivery of a charged agent from an electrotransport delivery device (10) through a body surface at higher electrotransport agent delivery efficiency (E) defined by the agent delivery rate per unit of applied current; the device (10) having a donor reservoir (26, 46) containing the agent and having a delivery area, and having a source of electrical power (32) and a current controller (19, 40), the method being characterized by the steps of:

adapting the current controller (19, 40) to provide an applied pulsing DC current having a periodic current waveform, a pulsing frequency, and a duty cycle, the pulsing current applied to the reservoir (26, 46) and to the body surface, wherein an applied current density is defined by the applied pulsing current divided by the delivery area, and wherein a higher electrotransport agent delivery efficiency (E) state is induced in the body surface when the applied current density is greater than or equal to a critical current density level ($I_c$) and the applied pulsing current is applied for greater than or equal to a critical time period ($t_c$).

15. The method of claim 14, wherein the agent delivery efficiency (E) is more stable at a current density above the critical level ($I_c$) and less stable at a current density below the critical level ($I_c$).

16. The method of claim 14, wherein the device is adapted to be applied to human skin, and the controller (19, 40) provides an applied current density at least about 40 $\mu A/cm^2$.

17. The method of claim 14, wherein the agent is fentanyl, and the controller (19, 40) provides an applied current density of at least 40 $\mu A/cm^2$ for at least about 10 msec.

18. The method of claim 14, wherein the pulsing frequency is less than about 100 Hz.

19. The method of claim 14, wherein the pulsing frequency less than about 10 Hz.

20. The method of claim 14, wherein the duty cycle is less than about 100%.

21. The method of claim 14, wherein the body surface comprises intact human skin and $I_c$ is at least about 40 $\mu A/cm^2$.

22. The method of claim 14, wherein the agent is fentanyl, the body surface is intact human skin, and the applied pulsing current is equal to $I_c$ which is at least about 40 $\mu A/cm^2$, and wherein the pulsing current is applied for at least about 10 msec.

23. The method of claim 14, wherein the agent is goserelin, and the applied pulsing current is at least about 50 $\mu A/cm^2$, and wherein the pulsing current is applied for at least about 10 msec.

24. The method of claim 14 further including the step of varying the duty cycle and the agent delivery rate.

25. The method of claim 14 further including the step of varying the pulsing frequency and the agent delivery rate.

26. The method of claim 14 further including the step of adding a suitable competitive specie to the donor reservoir (26, 46).

* * * * *

UNITED STATES PATENT AND TRADEMARK OFFICE
CERTIFICATE OF CORRECTION

PATENT NO.        : 7,212,853 B1
APPLICATION NO.   : 08/952368
DATED             : May 1, 2007
INVENTOR(S)       : Phipps et al.

It is certified that error appears in the above-identified patent and that said Letters Patent is hereby corrected as shown below:

Column 6,
Line 42, delete "(Id)" and insert -- $(I_d)$ --.

Column 7,
Line 30, delete "IC" and insert -- $I_c$ --.

Column 14,
Line 7, delete "antspasmodics" and insert -- antispasmodics --.

Column 15,
Line 35 and 36, delete "(=100µA 5 cm$^2$)." and insert -- (=100 µA ÷ 5 cm$^2$). --.

Signed and Sealed this

Eighteenth Day of August, 2009

David J. Kappos
*Director of the United States Patent and Trademark Office*